United States Patent [19]
Ben-Hur

[11] Patent Number: 6,090,599
[45] Date of Patent: Jul. 18, 2000

[54] VIRAL INACTIVATION TREATMENT OF RED BLOOD CELLS USING PHTHALOCYANINES AND RED LIGHT

[75] Inventor: Ehud Ben-Hur, New York, N.Y.

[73] Assignee: New York Blood Center, Inc., New York, N.Y.

[21] Appl. No.: 09/068,230

[22] PCT Filed: Nov. 4, 1996

[86] PCT No.: PCT/US96/17528

§ 371 Date: Sep. 1, 1998

§ 102(e) Date: Sep. 1, 1998

[87] PCT Pub. No.: WO97/16966

PCT Pub. Date: May 15, 1997

Related U.S. Application Data

[60] Provisional application No. 60/007,306, Nov. 6, 1995.

[51] Int. Cl.$^7$ .............................. C12N 13/00; C12N 7/04; A61M 37/00
[52] U.S. Cl. .......................... 435/173.3; 435/2; 435/236; 604/4; 540/145
[58] Field of Search .................................... 540/122, 135; 604/4; 435/173.3, 236

[56] References Cited

U.S. PATENT DOCUMENTS

| | | | |
|---|---|---|---|
| 4,878,891 | 11/1989 | Judy et al. | 604/5 |
| 5,109,016 | 4/1992 | Dixon et al. | 514/410 |
| 5,120,649 | 6/1992 | Horowitz et al. | 435/173 |
| 5,232,844 | 8/1993 | Horowitz et al. | 435/173.1 |
| 5,238,940 | 8/1993 | Liu et al. | 514/410 |
| 5,281,616 | 1/1994 | Dixon et al. | 514/410 |
| 5,407,808 | 4/1995 | Halling et al. | 435/34 |
| 5,484,778 | 1/1996 | Kenney et al. | 514/63 |
| 5,484,803 | 1/1996 | Richter et al. | 514/410 |
| 5,516,629 | 5/1996 | Park et al. | 435/2 |
| 5,556,612 | 9/1996 | Anderson et al. | 424/59 |
| 5,705,518 | 1/1998 | Richter et al. | 514/410 |

OTHER PUBLICATIONS

D.L. Terrian, "The photochemistry and photobiology of rhodium(III) ploypyridyl complexes and psoralen pro-drugs", Diss. Abstr. Inter'l. 58(3B):1276 (1996).

Ben–Hur et al., Photochem and Photobiol., vol. 62, No. 3., pp. 383–388, 1995.

Rywkin et al., Photochem and Photobiol., vol. 60., No. 2., pp. 165–170., 1994.

*Primary Examiner*—Richard L. Raymond
*Assistant Examiner*—Pavanaram K Sripada
*Attorney, Agent, or Firm*—Amster, Rothstein & Ebenstein

[57] ABSTRACT

Disclosed are two processes. The first process involves treating a red blood cell-containing composition to inactivate an extracellular or intracellular virus which may be present in said red blood cell-containing composition by subjecting said red blood cell-containing composition to a virucidally effective amount of a phthalocyanine and red light, wherein the improvement involves (i) determining the action spectrum of said phthalocyanine for causing inactivation of said virus; (ii) determining the action spectrum of said phthalocyanine for causing red blood cell damage; (iii) comparing (i) and (ii), and, if (i) and (ii) are not identical then determining the wavelength at which the largest favorable difference exists between (i) and (ii); (iv) providing a red light source emitting red light only in 10 nm in either direction of the wavelength determined in (iii); and then (v) subjecting said red blood cell-containing composition to said virucidally effective amount of said phthalocyanine and said provided red light source. In a preferred embodiment, the phthalocyanine is Pc 4, which has the formula: $HOSiPcOSi(CH_3)_2(CH_2)_3N(CH_3)_2$. The second process involves transfusing red blood cells to a patient in need thereof by withdrawing red blood cells from a donor, subjecting the red blood cells to the first process and transfusing the red blood cells to said patient.

7 Claims, 3 Drawing Sheets

Pc 4

VIRAL INACTIVATION TREATMENT OF RED BLOOD CELLS USING PHTHALOCYANINES AND RED LIGHT

Provisional application Ser. No. 60/007,306 Nov. 6, 1995. This application is a 371 of PCT/US96/17528 filed Nov. 4, 1996.

This work is supported in part by award no. 2RO1-HL41221 from the National Heart, Lung and Blood Institute and award no. PO1-CA48735 from the National Cancer Institute.

BACKGROUND OF THE INVENTION

1. Field of the Invention

The present invention concerns a process for rendering a red blood cell-containing composition substantially free of an extracellular or intracellular virus which may be present therein without substantially disrupting the red blood cells or labile proteins or other valuable biological components also contained therein.

2. Description of the Related Art

The use of blood for transfusion is safer nowadays than it has ever been. This is particularly true for coagulation factor concentrates and plasma. These blood products have been made completely safe with respect to transmission of hepatitis B virus (HBV), hepatitis C virus (HCV) and human immunodeficiency virus (HIV) by implementation of virucidal procedures. See B. Cuthbertson et al., "Viral contamination of human plasma and procedures for preventing virus transmission by plasma products," In: *Blood Separation and Plasma Fractionation*, ed. by R. J. Harris, Wiley-Liss, New York, 1991, pages 385–435; and A. M. Prince et al., *Eur. J. Epidemiol.*, 3: 103–118 (1987).

However, transfusion of cellular blood components is still associated with risk of infection in spite of improvement in donor selection and serological testing. See P. Kuhnl et al., "Reduction of virus load in blood donations by screening methods," In: *Virus Inactivation in Plasma Products*, ed. by J. J. Morganthaler, Karger Press, Basel, 1989, pages 9–22. As a result, efforts are now focused on sterilizing red blood cell (RBC) and platelet concentrates. The most promising results were obtained with the use of photochemical approaches. For a recent review, see E. Ben-Hur and B. Horowitz, "Advances in photochemical approaches for blood sterilization," *Photochem. Photobiol.*, 62: 383–388 (1995).

For virus inactivation in RBC concentrates use has been made of phthalocyanines. See, B. Horowitz et al., "Inactivation of viruses in blood with aluminum phthalocyanine derivatives," *Transfusion*, 31: 102–108 (1991); and E. Ben-Hur et al., "Photodynamic inactivation of retroviruses by phthalocyanines: the effect of sulfonation, metal ligand and fluoride," *J. Photochem. Photobiol. B:Biol.*, 13: 145–152 (1992).

The phthalocyanines are efficient photodynamic sensitizers with maximum absorption in the far red (650–700 nm). Virus inactivation appears to be mediated by disruption of the virus envelope. See Z. Smetana et al., "Photodynamic inactivation of herpes viruses with phthalocyanine derivatives," *J. Photochem. Photobiol. B:Biol.*, 22: 37–43 (1994).

However, the RBC membrane can also be damaged in the process. See E. Ben-Hur et al., "Photohemolysis of human erythrocytes induced by aluminum phthalocyanine tetrasulfonate," *Cancer Lett.*, 30: 321–327 (1986); and E. Ben-Hur et al., "Inhibition of phthalocyanine-sensitized photohemolysis of human erythrocytes by quercetin," *Photochem. Photobiol.*, 57: 984–988 (1993).

Thus, it was necessary to enhance the specificity of the process. This was achieved by various approaches. First, structure-activity relationships were sought. See E. Ben-Hur et al., "Phthalocyanine-induced photohemolysis: structure-activity relationship and the effect of fluoride," *Photochem. Photobiol.*, 58: 351–355 (1993); and S. Rywkin et al., "New phthalocyanines for photodynamic virus inactivation in red blood cells," *Photochem. Photobiol.*, 60: 165–170 (1994). The result was the identification of a silicon phthalocyanine Pc 4 having maximal virucidal activity and minimal RBC damage. See E. Ben-Hur et al., "Virus inactivation in red cell concentrates by photosensitization with phthalocyanines: protection of red cells but not of vesicular stomatitis virus with a water-soluble analogue of vitamin E," *Transfusion*, 35: 401–406 (1995).

Second, quenchers of reactive oxygen species were added during light exposure. These include mannitol [S. Rywkin et al., "Importance of type I and type II mechanisms in the photodynamic inactivation of viruses in blood with aluminum phthalocyanine derivatives," *Photochem. Photobiol.*, 56: 463–469 (1992)], glutathione [S. Rywkin et al., "Selective protection against IgG binding to red cells treated with phthalocyanines and red light for virus inactivation," *Transfusion*, 35: 414–420 (1995)] and Trolox™ [E. Ben-Hur et al., "Virus inactivation in red cell concentrates by photosensitization with phthalocyanines: protection of red cells but not of vesicular stomatitis virus with a water-soluble analogue of vitamin E," *Transfusion*, 35: 401–406 (1995)]. These quenchers protect against RBC damage but have no effect on virus inactivation.

Third, light irradiance was increased based on the finding that at high fluence rates there is less RBC damage. See, E. Ben-Hur et al., "The effect of irradiance on virus sterilization and photodynamic damage in red blood cells sensitized by phthalocyanines," *Photochem. Photobiol.*, 61: 190–195 (1995). Virus inactivation is not affected by the irradiance.

In spite of these advances, there continues to be a need to enhance the specificity of the process.

SUMMARY OF THE INVENTION

All of the previous work in this field was done with broad band light sources, i.e., light sources emitting light across a broad wavelength band of 600–800 nm.

Recently, we observed that when using a narrow band light (668 nm), corresponding to the absorption maximum of Pc 4 in solution, RBC damage at equivirucidal doses was considerably higher compared to broad band light (our own unpublished results). A possible explanation for this is that the action spectrum for RBC damage is shifted with respect to that of virus inactivation.

We therefore determined the efficiency of monochromatic light in the relevant range (660–700 nm) for Pc 4-induced RBC damage and viral inactivation. The results showed that the action spectra for these different endpoints do not overlap. We therefore discovered a range of wavelengths where virus kill can be achieved with reduced damage to RBC.

The foregoing suggested a general process for enhancing the specificity of the process.

Accordingly, one embodiment of the present invention relates to a process for treating a red blood cell-containing composition to inactivate an extracellular or intracellular virus which may be present in said red blood cell-containing composition, said process comprising subjecting said red blood cell-containing composition to a virucidally effective amount of a phthalocyanine and red light, wherein the improvement comprises:

(i) determining the action spectrum of said phthalocyanine for causing inactivation of said virus;

(ii) determining the action spectrum of said phthalocyanine for causing red blood cell damage;

(iii) comparing (i) and (ii), and, if (i) and (ii) are not identical, then determining a wavelength at which the largest favorable difference exists between (i) and (ii);

(iv) providing a red light source emitting red light substantially only in 10 nm in either direction of the wavelength determined in (iii); and then (v) subjecting said red blood cell-containing composition to said virucidally effective amount of said phthalocyanine and said provided red light source.

By the phrase "the wavelength at which the largest favorable difference exists", we mean the wavelength at which the highest level of virus kill can be achieved with the lowest level of red cell damage.

By the phrase "substantially only", we mean 50%, preferably greater than 70–80%, most preferably 90% of the light emitted from said red light source is within the recited wavelength range.

Another embodiment of the present invention relates to a process for treating a red blood cell-containing composition to inactivate an extracellular or intracellular which may be present in said red blood cell-containing composition, said process comprising subjecting said red blood cell-containing composition to a virucidally effective amount of Pc 4, which has the formula: $HOSiPcOSi(CH_3)_2(CH_2)_3N(CH_3)_2$, and red light, wherein the red light is provided by a light source emitting red light substantially only in a wavelength range of from about 690 nm to about 700 nm.

Another embodiment of the present invention relates to a process for transfusing red blood cells to a patient in need thereof, said process comprising withdrawing red blood cells from a donor, subjecting the red blood cells to one of the processes in the preceding paragraphs and transfusing the red blood cells to said patient.

BRIEF DESCRIPTION OF THE DRAWINGS

The invention will now be described with reference to the drawings wherein.

DETAILED DESCRIPTION OF THE INVENTION

Figure 1:
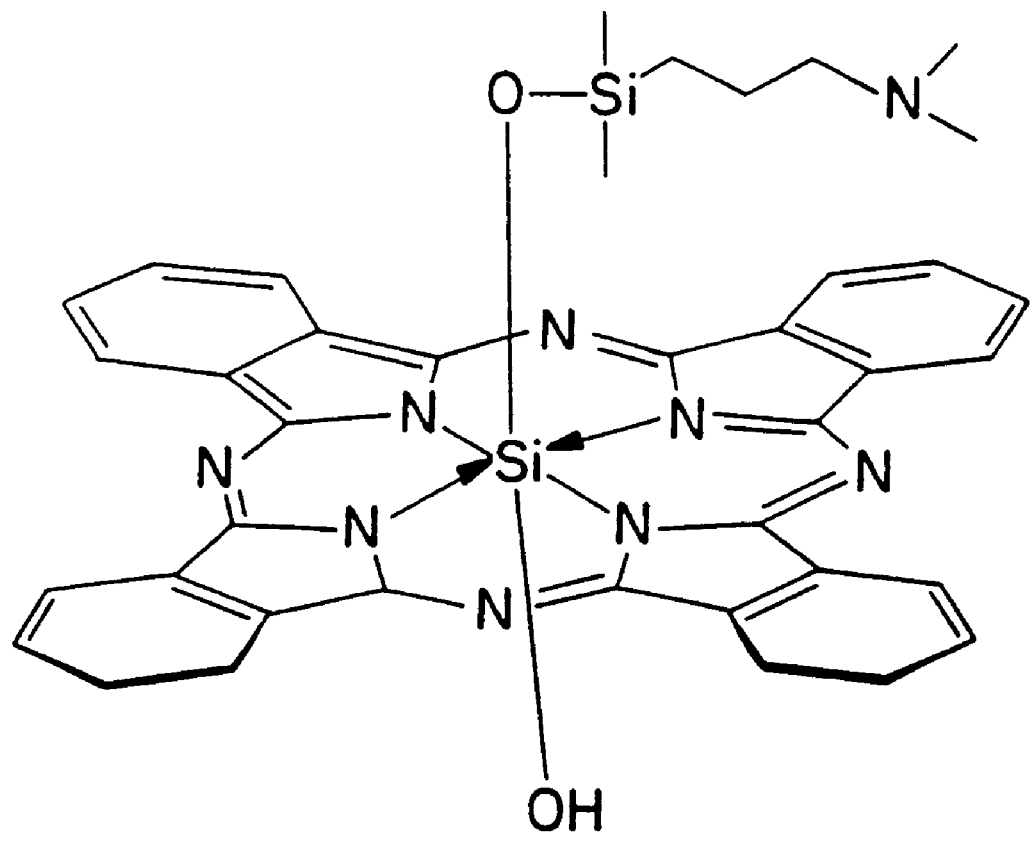
FIG. 1 depicts the chemical structure of Pc 4 [$HOSiPcOSi(CH_3)_2(CH_2)_3N(CH_3)_2$].

Details of viral, and blood borne parasite, inactivation using photosensitizer compounds, e.g., phthalocyanines, and light are not repeated here, these details being well known to those of ordinary skill in the art, for example, from U.S. Pat. No. 5,120,619, U.S. Pat. No. 5,232,844, U.S. Ser. No. 08/031,787, filed Mar. 15, 1993, U.S. Ser. No. 08/364,031, filed Dec. 23, 1994, U.S. Ser. No. 08/344,919, filed Nov. 25, 1994, U.S. Ser. No. 08/081,774, filed Jun. 23, 1993, U.S. Ser. No. 08/191,907, filed Feb. 4, 1994, U.S. Ser. No. 08/340,557, filed Nov. 16, 1994, U.S. Ser. No. 08/444,648, filed May 19, 1995, and U.S. Ser. No. 08/413,054, filed Mar. 29, 1995, the entire contents of all of which are hereby incorporated by reference.

The term "red blood cell-containing composition", as used herein, is not to be construed to include any living organism. The inventive process is carried out ex vivo, although the treated red blood cell-containing composition will be used in vivo.

Red blood cell-containing compositions include, but are not limited to, whole blood, fetal cord blood and red blood cell concentrates.

With respect to the phthalocyanine, any phthalocyanine can be used, but preference is given to zinc tetrasulfonate, tetrasulfophthalocyanine, aluminum tetranitrophthalocyanine, zinc tetranitrophthalocyanine, tetracarboxyphthalocyanine, GaCl-, AlCl- or Ga-tetrasulfophthalocyanine, and GaCl-, AlCl- or Ga-tetrasulfophthalocyanine, and the like. Most preferably, the phthalocyanine is Pc 4 [$HOSiPcOSi(CH_3)_2(CH_2)_3N(CH_3)_2$].

With respect to the red light, a typical light fluence range is 5 to 150 $J/cm^2$, most preferably 10 to 50 $J/cm^2$.

Irradiation times range from 1 to 240 minutes, most preferably 5 to 120 minutes.

Where Pc 4 is used, any narrow band light source centered at approximately 695 nm is sufficient. By "narrow" is meant approximately 10 mn, preferably 5 nm, in either direction from center. Examples of such narrow band light sources include, but are not limited to, light emitting diodes and diode lasers.

As noted above, the treatment with the phthalocyanine and red light is optionally conducted in the presence of quencher compounds. When utilized, suitable quencher compounds are any substances known to react with free radicals (so-called "type I quenchers") and reactive forms of oxygen (so-called "type II quenchers"). Representative quenchers include, but are not limited to, unsaturated fatty adds, reduced sugars, cholesterol, indole derivatives, and the like, azides, such as sodium azide, tryptophan, polyhydric alcohols, such as glycerol and mannitol, thiols, such as glutathione, superoxide dismutase, flavonoids, such as quercetin and ritin, amino adds, 1,4-diazabicyclo[2.2.2]octane (DABCO), vitamins, such as vitamin A, C and E, and the like. Preferably, the quencher compound is selected from the group consisting of glutathione, mannitol, quercetin, rutin, vitamin E, and Trolox™ (6-hydroxy-2,5,7,8-tetramethylchroman-2-carboxylic acid), and mixtures thereof, especially, as will be explained below, mixtures thereof calculated to quench both type I and type II reactions.

The quencher is used in conventional quenching amounts, as known, for example, from the above-mentioned patents and applications. The quencher is especially beneficial when used in an amount of from 2 to 10 mM.

Superior virus kill is achieved by quenching both type I and type II photodynamic reactions, i.e., by using a mixture of type I and type II quenchers or by using compounds, e.g., flavonoids, that are known by themselves to quench both type I and type II reactions. The range of virus kill is in most cases broader than that achieved by using type I or type II quenchers alone—even as compared to increased concentrations of the type I or type II quencher—or by using mixtures of type I quenchers or mixtures of type II quenchers. Moreover, this broader range of virus kill is achieved without sacrificing intact cell functionality or structure.

The inventive process is typically carried out over a temperature range of 0–42° C., preferably 15–37° C., and most preferably 15–25° C.

The inventive process is typically carried out a pH 6.5–8, preferably pH 7.2–7.6.

Samples are subjected to the inventive process for a period of time that is typically less than 24 hours.

Samples are typically liquid, but it is also possible to treat frozen samples.

Using the inventive process, it is possible to inactivate both lipid coated, human pathogenic viruses and non-enveloped viruses, as well as other pathogens. Non-limiting examples of such viruses are set forth in the abovementioned patents and applications. Advantageously, hepatitis B viruses (HBV), hepatitis C viruses (HCV) or human immunodeficiency viruses (HIV) are inactivated.

Using this viral inactivation process, it is possible to inactivate at least $10^4$, preferably $10^6$, infectious units of such viruses or other pathogens, for example, blood borne parasites, while at the same time red blood cells in the composition that is treated are protected from substantial disruption or inactivation.

In the case of red blood cells, the lack of substantial disruption or inactivation can be ascertained by measuring the structural integrity of the treated red blood cells. Where structural integrity has been compromised, hemoglobin will be lost. Accordingly, the retention of hemoglobin as a result of the treatment serves as a good gauge of the amounts of treated cells that remain intact.

Thus, for example, if 20% of the red blood cells are disrupted by the treatment, then likewise 20% of the hemoglobin will be lost. In other words, if 80% of the hemoglobin is retained after the treatment, then 80% of the red blood cells remain structurally intact.

The quantity of hemoglobin in the red blood cells, before and after treatment, can be measured according to conventional techniques.

The red blood cell-containing compositions treated according to the invention, while initially containing as much as $\geq 1000$ infectious units of virus/L, after the virus has been inactivated and treatment according to the invention has been conducted, have a retention of intact cell structure of greater than 70%, preferably greater than 80% and most preferably greater than 95%.

Moreover, particularly when the treatment with the phthalocyanine and red light is carried out in the presence of vitamin E or some derivative thereof, for example, Trolox™ (6-hydroxy-2,5,7,8-tetramethylchroman-2-carboxylic acid), the red blood cells in the treated sample are characterized by a reduced leakage of $K^+$ and loss of negative charges from the cell membrane. Particularly, after prolonged storage, such treated red blood cells showed a marked reduction in the leakage of $K^+$.

Although the main objective was to protect red blood cells, the inventive process is also protective of other blood cells, for example, platelets, and also proteins contained in blood, for example, coagulation factors, e.g., Factor VIII, lymphokines, etc.

The invention will now be further described with reference to the following non-limiting examples:

EXAMPLES

Materials and Methods

1. Chemicals

Pc 4 [HOSiPcOSi(CH$_3$)$_2$(CH$_2$)$_3$N(CH$_3$)$_2$] was synthesized as described previously [Oleinick et al., "New phthalocyanine photosensitizers for photodynamic therapy," *Photochem. Photobiol.*, 57: 242–247 (1993)] and further purified with high performance liquid chromatography. Its purity was 98.5%. Pc 4 was formulated in Cremophor emulsion [Ben-Hur et al., "Biodistribution and virus inactivation efficacy of the silicon phthalocyanine Pc 4 in red blood cell concentrates as a function of delivery vehicle," *Photochem. Photobiol.*, 62: 575–579 (1995)] at a concentration of 0.4 mM and stored at −20° C. prior to use.

Trolox™ (6-hydroxy-2,5,7,8-tetramethylchroman-2-carboxylic acid) was obtained from Aldrich Chemical Co. (Milwaukee, Wis.) and stored as 0.1M aqueous solution at 4° C.

Glutathione and mannitol were from Sigma Chemical Co. (St. Louis, Mo.) and were made up fresh as 0.2M solutions in phosphate buffered saline (PBS) prior to use.

2. Biologicals

Red blood cell (RBC) concentrate (70% hematocrit) was obtained from the New York Blood Center and was used as such for vesicular stomatis virus (VSV) inactivation. For RBC damage production the RBC concentrate was diluted 1 in 1 with PBS.

Human A549 cells were obtained from the American Type Culture Collection (Rockville, Md.).

VSV was initially obtained from Dr. W. Stewart, Sloan Kettering Memorial Hospital, New York, N.Y., and was cultured in A549 cells.

3. Light Source and Exposure

The light source was an argon-ion laser, model Innova 100™ (Coherent, Palo Alto, Calif.) pumping a dye laser with circulating DCM dye ([2-[2-[4-(dimethylamino) phenyl] ethenyl]-6-methyl-4H-pyran-4-ylidene[-propanedinitrile]) (Exciton Inc., Dayton, Ohio). The light was delivered to the samples via a 400 μm fiber optic terminated with a microlens forming a homogenous beam of 5 cm diameter. The wavelength was tuned over 660–700 nm, as determined by a spectrograph. The light irradiance was 10 mW/cm$^2$.

Samples of 3 ml RBC concentrate were irradiated in 35-mm Petri dishes with continuous stirring. At intervals, aliquots were withdrawn for assay of VSV infectivity or RBC damage.

4. Assay of VSV Infectivity

The infectivity of VSV was assayed as described by Horowitz et al., "Inactivation of viruses in blood with aluminum phthalocyanines," *Transfusion*, 31: 102–108 (1991).

Briefly, VSV was added to the RBC concentrate to a final titer of about $10^6$ infectious units per ml. The RBC concentrate contained Pc 4 at 2 μm concentration and the quenchers Trolox™ (6-hydroxy-2,5,7,8-tetramethylchroman-2-carboxylic acid), glutathione and mannitol at concentrations of 5, 4 and 4 mM, respectively.

After 30 min at room temperature in the dark the samples were irradiated and 0.2 ml aliquots were diluted 10-fold with Dulbecco's modified Eagle's medium containing 5% fetal calf serum and centrifuged to remove RBC. The supernatants were sterile-filtered through 0.22 μm filters (Millipore, Bedford Mass.) and stored at −80° C.

For assay, the samples were serially diluted 10-fold, inoculated into A549 cell cultures in 96-well microtiter plates, and incubated at 37° C. in a $CO_2$ incubator for 72 hours. Cellular pathology was then scored in the wells for eight replicates of each dilution, and the viral titer was quantitated by the Spearman-Karber method [C. Spearman, "The method of right and wrong cases (constant stimuli) without Gauss formulae," *Br. J. Psychol.*, 2: 227–242 (1908) .] Experiments were repeated twice with no significant differences.

5. RBC Binding to Poly-L-lysine

The reduction of negative surface charges on RBC as a result of photosensitization was assayed by measuring RBC binding to poly-L-lysine (PLL) as described previously by S. Rywkin et al., "New phthalocyanines for photodynamic virus inactivation in red blood cells," *Photochem. Photobiol.*, 60: 165–170 (1994).

Briefly, RBC concentrate was diluted 2-fold in PBS and Pc 4 was added at 2 $\mu$M concentration. After 30 min in the dark samples of 3 ml were irradiated and 0.1 ml aliquots were withdrawn at intervals. The aliquots were diluted 500-fold in PBS and 1 ml was added to a 35-mm Petri disk, precoated with PLL. After 1 hour at room temperature the dishes were rinsed with PBS to remove unbound cells. The adsorbed cells were lysed with 2 ml of distilled water and the absorbance of the lysate was measured at 415 nm in a spectrophotometer to quantitate the hemoglobin in bound cells. Results (average of triplicates per datum point) were calculated as percentage of untreated control. Standard errors of the mean were less than 5%.

6. Calculation of Relative Efficiency

The relative efficiency of each wavelength for VSV inactivation was calculated by determining the light dose required for 1.5 $\log_{10}$ kill. The reciprocal of this dose is the rate of inactivation. The rate calculated for each wavelength was normalized to that obtained at 670 nm, set as 1. For RBC damage the light dose required for 50% reduction of bound cells was determined and the relative efficiency was then calculated as above. The light dose at each wavelength was adjusted for photon energy h$\nu$.

7. Absorption Spectrum of Pc 4 Bound to RBC

To obtain the absorption spectrum of Pc 4 when bound to RBC, advantage was taken of the fact that essentially all of the dye is bound to RBC membranes. Therefore, Pc 4 at 10 $\mu$M was added to RBC concentrate and RBC membranes were then isolated as described by Zuk et al., "High-performance liquid chromatography determination of the silicon phthalocyanine Pc 4 in human blood," *J. Chromatogr. Biomed. Appl.* (1995, in press).

Briefly, a 10 ml sample of RBC suspended in PBS at 50% hematocrit was diluted with 5 ml of 10 mM Tris-HCl, pH 7.4, and 30 ml of 0.1 mM EGTA (ethylene glycol-bis($\beta$-aminoethyl ether)-N,N,N',N'-tetraacetic acid). The resulting lysate was centrifuged and the membrane pellet was resuspended in the lysing solution and centrifuged. This was repeated a few times until the membranes were white.

Under these conditions over 97% of Pc 4 present in RBC is recovered from the membranes. The membranes were suspended in PBS and the absorption spectrum of Pc 4 was recorded on a spectrophotometer using RBC membranes with Pc 4 as a blank.

RESULTS

Figure 2:
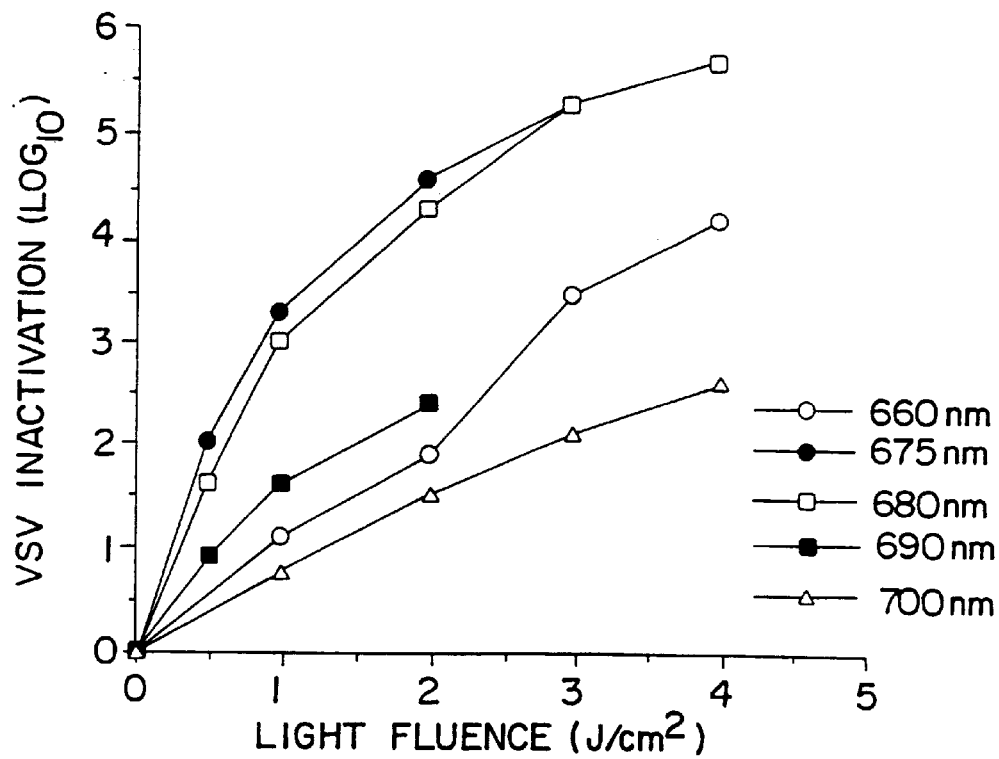
FIG. 2 is a graph depicting Pc 4-induced vesicular stomatis virus (VSV) inactivation at various wavelengths. Red blood cell (RBC) concentrates were inoculated with VSV and exposed to laser light at the wavelengths indicated in the presence of Pc 4 at 2 $\mu$M.

FIG. 2 shows Pc 4-induced VSV inactivation as a function of light fluence at various wavelengths. Inactivation rate was linear with dose up to about 2 $\log_{10}$. Therefore, for calculation of relative efficiency we used the dose resulting in 1.5 $\log_{10}$ kill.

Figure 3:
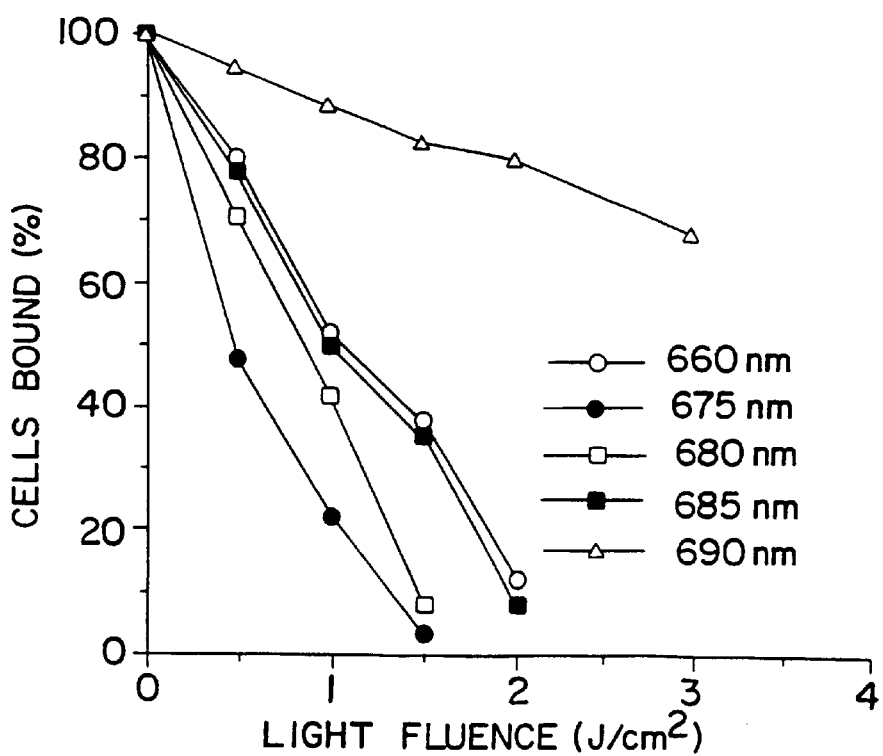
FIG. 3 is a graph depicting Pc 4-induced RBC damage at various wavelengths. RBC concentrates were exposed to laser light at the wavelengths indicated in the presence of Pc 4 at 2 $\mu$M.

The induction of RBC damage by Pc 4 at various wavelengths is shown in FIG. 3. RBC damage induction was linear with dose and varied widely with wavelength. At 695 and 700 nm RBC damage was barely discernible (data not shown).

Figure 4:
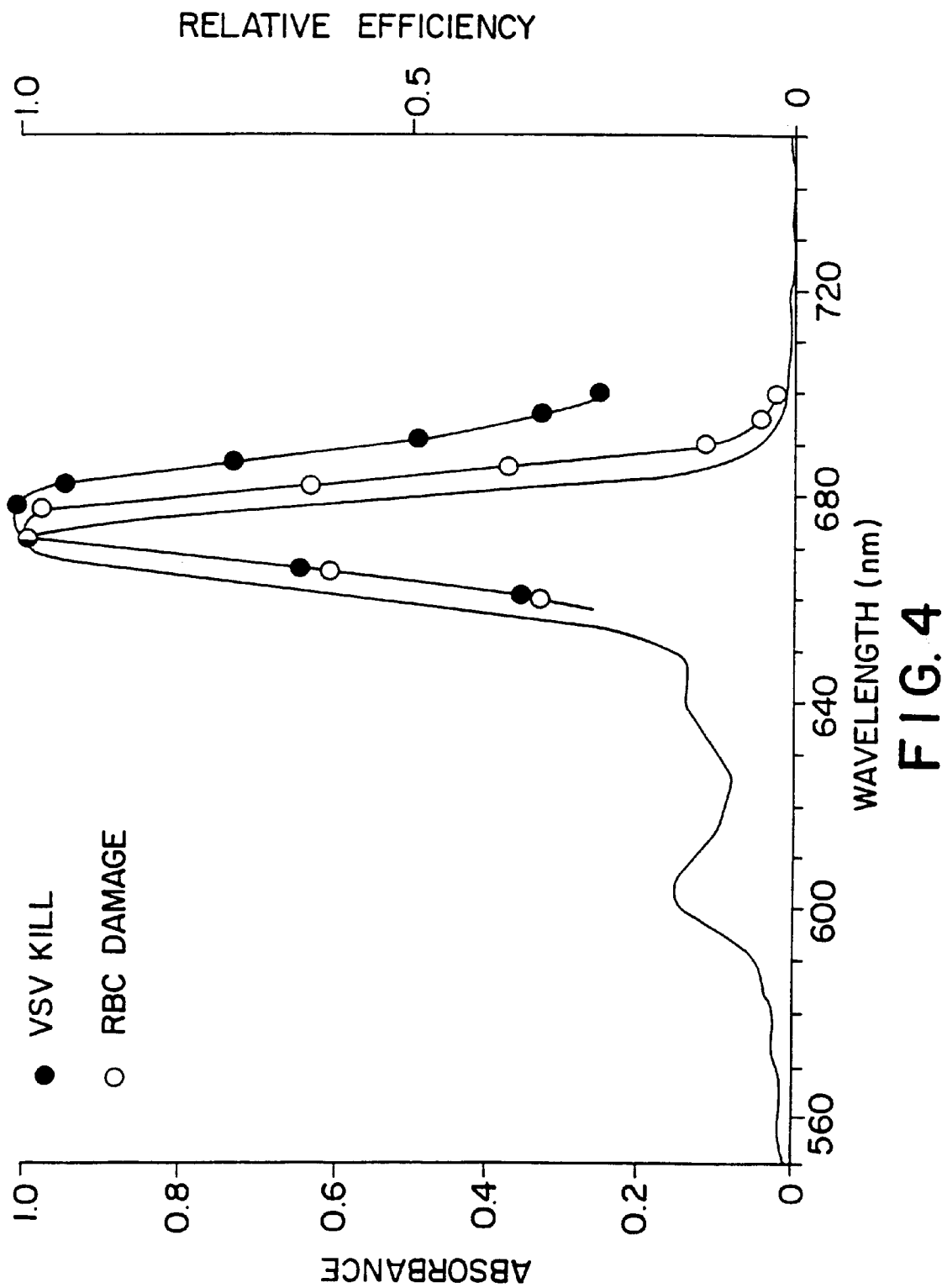
FIG. 4 is a graph depicting the action spectra of Pc 4-induced VSV inactivation and RBC damage superimposed on the absorption spectrum of Pc 4 in methanol.

The relative efficiency of VSV inactivation and RBC damage induction by Pc 4 over the wavelength range 660–700 nm at 5 nm intervals was calculated and plotted together with absorption of Pc 4 in solution (FIG. 4). Evidently, the various spectra are shifted with respect to each other. Such shifts must reflect the absorption spectra of Pc 4 when bound to its biological target. Indeed, when the absorption spectrum of Pc 4 bound to RBC membranes was recorded, $\lambda_{max}$ was red shifted by 5 nm to 673 nm.

Discussion

The foregoing results show that the action spectra for VSV inactivation and induction of RBC damage by Pc 4 are red shifted with respect to the absorption spectrum of Pc 4 in solution. This bathochromic shift is 4 nm for RBC damage and 10 nm for VSV inactivation at the maximum of the spectra. The difference between the action spectra is insignificant on the blue side of the curves and becomes pronounced on the red side, increasing with wavelength (FIG. 4). Thus, between 690 and 700 nm VSV inactivation is 4–10 times more efficient than RBC damage induction, depending on the wavelength.

A 5 nm red shift of phthalocyanine action spectrum with respect to its absorption spectrum in solution was first observed for aluminum phthalocyanine-induced (AlPc-induced) phototoxicity. See E. Ben-Hur et al., "Action spectrum (600–700 nm) for chloraluminum phthalocyanine-induced phototoxicity in Chinese hamster cells," *Lasers Life Sci*, 1: 79–86 (1986). Even larger red shifts (10–15 nm) were observed for the in vivo action spectra of aluminum phthalocyanine disulphonate ($AlPcS_2$) [G. Canti et al., "Action spectrum of photoactivated phthalocyanine $AlS_2Pc$ in tumor bearing mice," *Anti-Cancer Drugs*, 3: 139–142 (1992)] and zinc phthalocyanine tetrasulphonate ($ZnPcS_4$) [J. Griffiths et al., "On the photodynamic therapy action spectrum of zinc phthalocyanine tetrasulphonic acid in vivo," *J. Photochem. Photobiol. B:Biol.*, 24: 195–199 (1994)]. In principle, such shifts must reflect shifts of the absorption spectrum when the photosensitizer binds to its target molecule in vivo. However, a clear demonstration of this was provided in the case of $AlPcS_2$ only. See R. Cubeddu et al., "In vivo and in vitro absorption spectrum of disulphonated aluminum phthalocyanine in tumor bearing mice", In: *5th International Photodynamic Association Biennial Meeting*, ed. by A. Cortese, SPIE, Vol. 2371, Bellingham, Wash., 1995, pages 172–176.

In the present case, the absorption spectrum of Pc 4 in red cells was red shifted by 5 nm, closely corresponding to the action spectrum. The targets to which Pc 4 binds in RBC and VSV must differ considerably for the spectra to differ that much. For a further discussion of in vivo action spectra of photosensitizers for photodynamic therapy, see W. Star, "In vivo action spectra of photosensitizers for photodynamic therapy," *J. Photochem. Photobiol. B:Biol.*, 28: 101–102 (1995).

The finding here that the action spectrum of Pc 4-induced virus inactivation is red shifted with respect to that of RBC damage has important practical implications. There exists a range of wavelengths (690–700 nm) where virus kill can be achieved with little or no RBC damage, making RBC concentrate sterilization a viable commercial prospect with the use of an appropriate light source.

It seems reasonable that the phenomenon exists for other phthalocyanines. This can be confirmed for any phthalocyanine by following the teachings herein.

It will be appreciated that the instant specification and claims are set forth by way of illustration and not limitation, and that various modifications and changes may be made without departing from the spirit and scope of the present invention.

What is claimed is:

1. A process for treating a red blood cell-containing composition to inactivate an extracellular or intracellular virus which may be present in said red blood cell-containing composition, said process comprising contacting said red blood cell-containing composition with a virucidally effective amount of Pc 4, which has the formula: $HOSiPcOSi(CH_3)_2(CH_2)_3N(CH_3)_2$, and red light, wherein the red light is provided by a light source emitting greater than 80% of red light at a wavelength of about 690 nm to about 700 nm.

2. The process according to claim 1, wherein the red blood cell-containing composition is selected from the group consisting of whole blood, fetal cord blood and red blood cell concentrates.

3. The process according to claim 1, wherein the red blood cell-containing composition is subjected to said Pc 4 and red light in the presence of a quencher compound.

4. The process according to claim 3, wherein the quencher compound is selected from the group consisting of glutathione, mannitol, quercetin, rutin, vitamin E, and Trolox™ (6-hydroxy-2,5,7,8-tetramethylchroman-2-carbocylic acid), and mixtures thereof.

5. The process according to claim 4, wherein the quencher compound is Trolox™ (6-hydroxy-2,5,7,8-tetramethylchroman-2-carbocylic acid).

6. The process according to claim 1, wherein the red light source is a light emitting diode.

7. A process for transfusing red blood cells to a patient in need thereof, said process comprising withdrawing red blood cells from a donor, subjecting the red blood cells to the process according to claim 1 and transfusing the red blood cells to said patient.

* * * * *